United States Patent [19]

Pierson

[11] Patent Number: 5,951,294
[45] Date of Patent: Sep. 14, 1999

[54] METHOD OF CREATING AN INTERIM CROWN

[76] Inventor: Kenneth W. Pierson, 266 W. Fargo Ave., Hanford, Calif. 93230

[21] Appl. No.: 09/149,710

[22] Filed: Sep. 9, 1998

[51] Int. Cl.⁶ .................................................. A61C 5/08
[52] U.S. Cl. ............................................................. 433/218
[58] Field of Search .................................. 433/218, 219, 433/222.1, 223, 226, 204, 206, 212.1

[56] References Cited

U.S. PATENT DOCUMENTS

| | | | |
|---|---|---|---|
| 1,519,969 | 12/1924 | Bechtold | 433/218 |
| 1,609,549 | 12/1926 | Jaques, Jr. | 433/218 |
| 4,015,332 | 4/1977 | Manne | 433/219 |
| 5,332,390 | 7/1994 | Rosellini | 433/223 |
| 5,487,663 | 1/1996 | Wilson | 433/218 |
| 5,538,429 | 7/1996 | Mayclin | 433/218 |

OTHER PUBLICATIONS

"TRU–CHROME CROWNS", Rocky Mountain Dental Products Company, Denver, p.4, 1968.

*Primary Examiner*—Todd E. Manahan
*Attorney, Agent, or Firm*—Dennis B. Haase

[57] ABSTRACT

A method of restoring a damaged anterior tooth by creating an esthetically pleasing crown affixed thereto wherein a scaffold having an opening in the facial panel thereof, and having a cap fitted over the exterior thereof, is filled with a quantity of composite material and fitted to the tooth to be restored, which tooth had been previously prepared for receipt of said scaffold, and removing the cap once the composite material has cured, to reveal an aesthetically pleasing crown.

9 Claims, 4 Drawing Sheets

METHOD OF CREATING AN INTERIM CROWN

The present invention relates generally to restorative dentistry and, more particularly, to the interim restoration of a damaged anterior tooth, including a primary tooth, by a novel method of constructing an interim anterior crown having an especially esthetic appearance, and the crown itself.

BACKGROUND OF THE INVENTION

1. Field of the Invention

Over the years there has been an increasing recognition that dental patients of all ages, and particularly children who have not yet gotten their permanent teeth, pose substantially unique problems in the reconstruction of damaged anterior teeth. It is worthy of note that the American Dental Association recognizes pediatric dentistry as a specialty.

With respect to pre teen patients, primary teeth will inevitably be lost as permanent teeth push through, and it was once common to ignore decay and damage to such teeth. However, it has been recognized that care of one's teeth from very early stages of development compliments the growth and stability of permanent teeth. Since at least some baby teeth remain up to age 12, damage to such teeth has a deleterious effect both on the health of the child and the child's appearance.

While dental cavities are an ongoing problem, notwithstanding the advent of such ameliorating measures as fluoride, it is a rare person, including a pre teen, who does not fall or bump into something during the course of their existence, or otherwise in life's experiences has an accident which results in a damaged tooth, whether it be a crack in the enamel, a chip, or some other typical visually unpleasant damage, the repair of which becomes essential to health as well as self esteem.

Clearly health of the patient is a paramount consideration, but whether an adult, or a child in its formative years, self esteem, as a function of physical appearance, can not be discounted or overlooked. Whereas an adult will often opt for a more expensive restoration, primarily because of appearance, it is not uncommon for dentists to use the effective, but unattractive stainless steel restorations. There is increasing recognition, however, that appearance as a function of self esteem is important regardless of age.

As a consequence, there has been an increase in ongoing research relative to means of ameliorating the distractions that damage to an anterior tooth can present to a person. It is to the alleviation of this problem that the present invention is dedicated.

2. Overview of the Prior Art

The standard solution to the problem of a cracked, chipped or even broken anterior tooth has been to fit the damaged tooth with a stainless steel crown. In some cases, where the damage warranted more severe action, the tooth was actually extracted. Since teeth in younger patients are temporary in the sense that they will be lost in favor of a permanent tooth, the most economical approach suggests a minimum effort.

While a smile that flashes the gleam of metal, gold or steel, may, in some circles be a badge of distinction, for most patients, including children, it is at least disconcerting and when such gleam comes from an anterior tooth, it is more likely a distasteful and embarrassing distraction in one's appearance which can inhibit a smile, and detract from one's mood and, indeed, entire persona. It is important, therefore, that the dentist have available to him or her, an alternative that permits the patient to retain, if not heighten, his or her level of self esteem.

There have been some that have addressed the problem, among them, Wiedenfeld, who, in his U.S. Pat. No. 5,624,261 suggested a veneer constructed of a composite resin. The resin is, hopefully, adhered to a stainless steel crown, which is etched to provide a surface that will receive and hold the resin.

Another approach to the problem is found in U.S. Pat. No. 5,538,429 to Mayclin who, with apparent focus on costs, suggests much the same approach as Wiedenfeld, i.e., cementing an overlay over a steel crown. Mayclin deviates from Wiedenfeld in that the overlay is provided with openings to permit the thickness of the completed crown to be thickened to enhance durability.

The patent to Zelesnick, U.S. Pat. No. 2,031,996, is a 1936 offering that teaches the cutting of a window in the face of a steel crown. The essence of Zelesnick is the provision of two or more anchors 11 which are intended to be imbedded in a porcelain layer that fits in the window with its edges between the cap and the tooth being restored. In this manner, a white porcelain layer is fashioned in a steel crown, presumably to reduce the amount of metal that will be seen by others as the person wearing such a restoration talks or smiles. It will be evident to even the casual observer, however, that a crown is present, and at least some metal will be apparent.

Of less significance in the environment of the present invention, yet part of the overall picture of the art, are those patents which provide a framework within which bonding materials may work to adhere a non metallic cap to a metallic base.

Included in this art is the patent to Rieger, U.S. Pat. No. 4,846,718, which suggests a carrier cap, 12. Fung, in his U.S. Pat. No. 5,314,335 employs a wire mesh member 3, and Eldred U.S. Pat. No. 5,118, 296 teaches a chemical composition which he refers to as his cohesion layer.

Finally, Burgess et al., in their U.S. Pat. No. 4,668,193, provides holes 4, as contrasted perhaps to the window of Zelesnick, to permit the securing of a veneer. Burgess et al., however, is relevant only to posterior teeth, where appearance is less relevant and strength is vital.

As will become apparent from a reading of the forthcoming detailed description, none of these prior art efforts suggest the novel approach of the present invention.

SUMMARY OF THE INVENTION

The primary focus of the present invention is the provision of a method, at least on an interim basis, of effecting a cosmetic and structurally sound restoration of a damaged anterior tooth.

This is accomplished, in accordance with the present invention, by forming a specially designed crown in conformance with the profile of the damaged tooth. The crown is constructed by providing a scaffold which conforms to the tooth profile, and, additionally, is formed with a facial opening. The damaged tooth is prepared to receive a composite bonding material which will ultimately bond the crown to the tooth. To this end, the internal surface of the scaffold is also treated to enhance the capacity of the crown form to bond to the tooth.

A cap, preferable in the form of an acrylic matrix, is form fitted over the scaffold, and the crown form is partially filled with the bonding material and applied to the effected tooth. Apertures are formed in the cap to permit the excising of excess composite material.

Adherence to the foregoing procedure will inevitably result, when the composite material is cured about the crown and the cap is removed, in a restoration that closely proximates the appearance of a healthy tooth, thereby accomplishing the principal objective of the present invention.

Accordingly, it is another objective of the present invention to effect a cosmetically pleasing restoration of a damaged tooth in a manner which will not cause the young patient undue discomfort or require that he or she remain in an uncomfortable position for an extended period.

A further objective of the present invention is to effect the formation of a cosmetically pleasing crown for an anterior tooth which is structurally sufficient to withstand the use and abuse to which even a young patient might be likely to expose the crown during the normal activities of daily living without embarrassment or discomfort.

It is a distinct advantage, and thus another objective accomplished, by virtue of the ease with which the restoration of the present invention can be accomplished in a single visit, thus effecting further savings in time and money for the patient.

Yet another, and still further, objective of the present invention is to provide a restoration with all of the foregoing described attributes, at a cost which is less than the more conventional cast, or custom fit prosthesis, and is thus commensurate with the reality that the tooth being restored may not be permanent.

The foregoing, as well as other objectives and features will become apparent to those skilled in the art of restoration of anterior teeth from a reading of the following detailed description, taken in conjunction with the accompanying drawings, wherein:

IN THE DRAWINGS

DETAILED DESCRIPTION OF A PREFERRED EMBODIMENT

Figure 1:
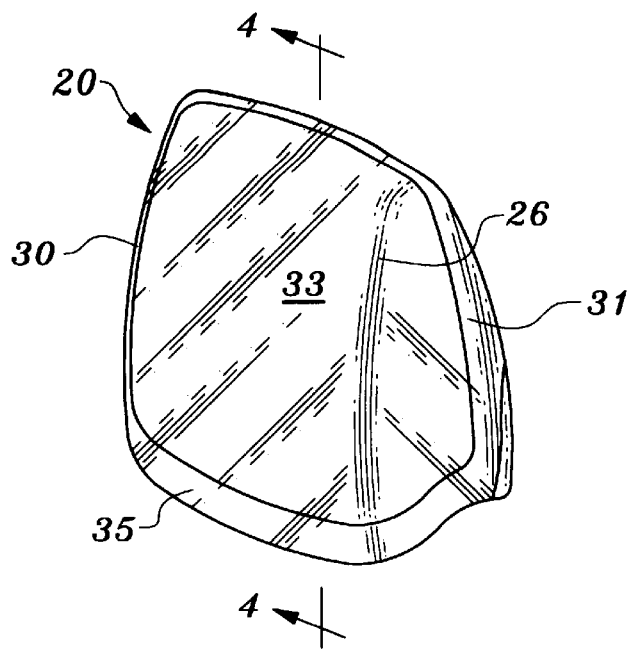
FIG. 1 is a perspective view of a completed crown formed in accordance with the present invention, about an anterior tooth to be restored, and featuring a formable scaffold, fashioned about the tooth and further illustrating a facial opening in the scaffold.
Figure 4:
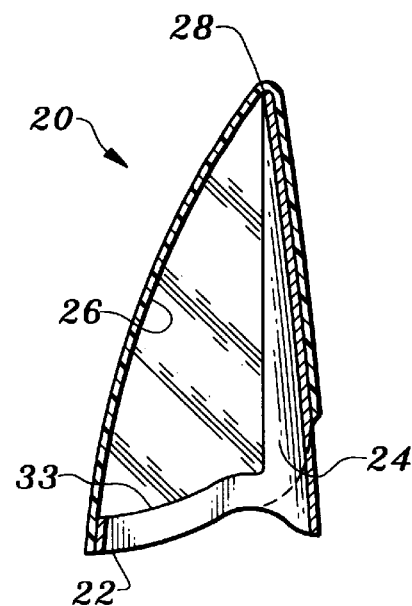
FIG. 4 is a sectional view taken along the lines 4—4 of FIG. 1, and illustrating the interrelationship of the various elements of the crown of the present invention.

With reference now to the drawings, and initially to FIGS. 1 through 4, an anterior crown, constructed in accordance with the present invention is illustrated from various angles, at 20.

In its preferred form, the crown 20 comprises a scaffold or envelope 22, constructed of a formable, non corrosive material such as stainless steel. The scaffold 22 is preformed to define a pocket which closely approximates the shape and size of an anterior tooth.

The scaffold is initially formed to its general configuration as previously referenced, such as to define a rearward or palatal panel 24, a facial panel 26, joined along a leading edge 28, and defining interproximal walls, or side panels 30 and 31, respectively.

Once the initial shape or profile of the scaffold is established, in order to provide a framework within which an esthetically pleasing facial panel can be constructed, there is formed, in accordance with one aspect of the invention, an opening 33 created in substantially the entire facial panel 26 of the scaffold, as perhaps best seen in FIG. 1, so as to define a substantial window in the facial panel, while maintaining structural integrity by providing a circumferential band 35 contiguous with the gum line of the patient and interconnecting the proximal sides 30 and 31. The specific scaffold is selected from several standard sizes, dependant on the size and shape of the tooth to be restored.

Having thus selected the structural framework from which the crown of the present invention is to be formed, the patient's tooth to be restored by the said crown is prepared by first removing all unstable material from the tooth which may be the consequence of decay or traumatic damage, and etching the surface of the tooth in any well known manner to better provide a bonding surface.

Figure 2:
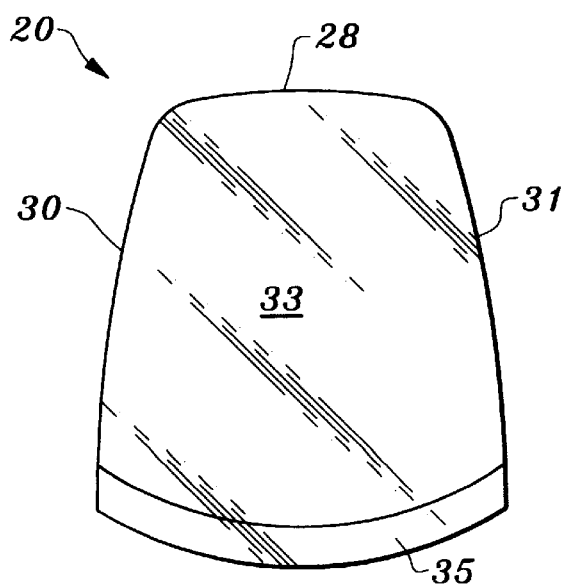
FIG. 2 is a front side elevation of the scaffold of FIG. 1.
Figure 3:
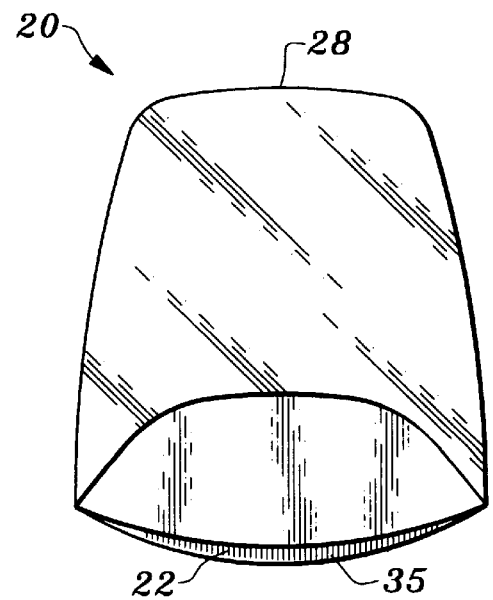
FIG. 3 is a rear elevation of the scaffold of FIG. 1.
Figure 5:
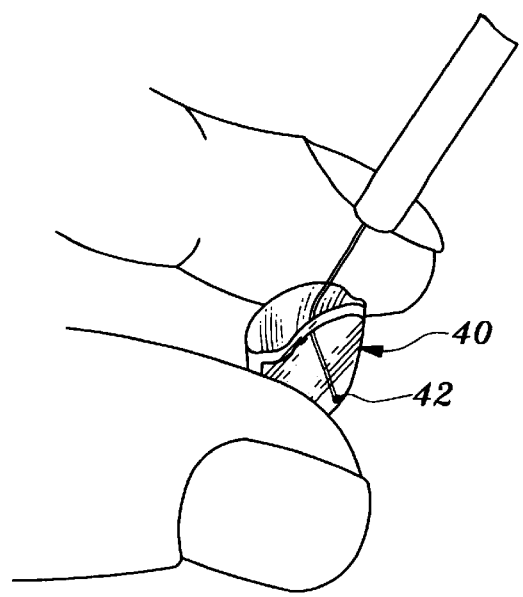
FIG. 5 illustrates the step of creating a vent in the cap to be fitted over the base member.
Figure 6:
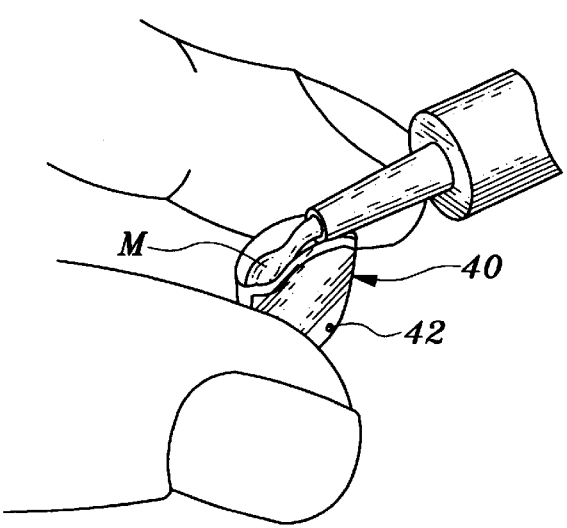
FIG. 6 illustrates the step of partially filling the crown form, with cap in place, with a composite material.

Next, an acrylic matrix, in the form of a cap 40, is provided which may be seen in FIGS. 2, 5 and 6. The cap 40 is necessarily pliant, and preferably of one of several well known acrylic materials currently in use in the field. The cap 40 is formed and trimmed to closely approximate the shape of the crown such that it can be snugly fitted over the scaffold during the course of formation of the crown of the present invention.

The next step in creating the subject crown is to either mix, or otherwise provide, a suitable quantity of a flowable dual-cure composite material M. The material may be colorized if necessary to, in accordance with this aspect of the invention, closely approximate the color of teeth of the patient immediately adjacent to the tooth to be restored. In this manner the restorative crown will blend into the overall appearance of the mouth and is distinguished by the casual observer's inability to discern the existence of a restoration.

As seen in FIG. 5, the cap 40 is prepared for receipt of the scaffold, and at least one, and preferably two, apertures or vent holes 42 are provided at or near the incisal corners of the cap, which will provide pressure relief and drainage of entrapped air and excess composite material in the later stages of formation of the crown.

Figure 7:
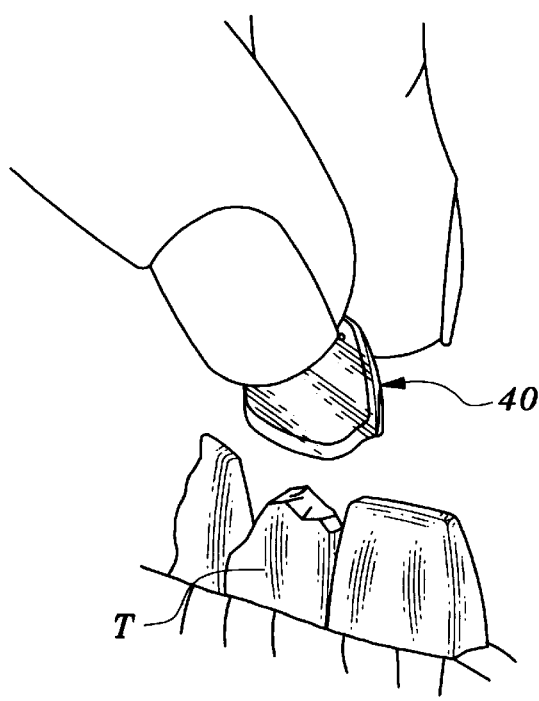
FIG. 7 illustrates the step of fitting the base member to the tooth to be restored.
Figure 8:
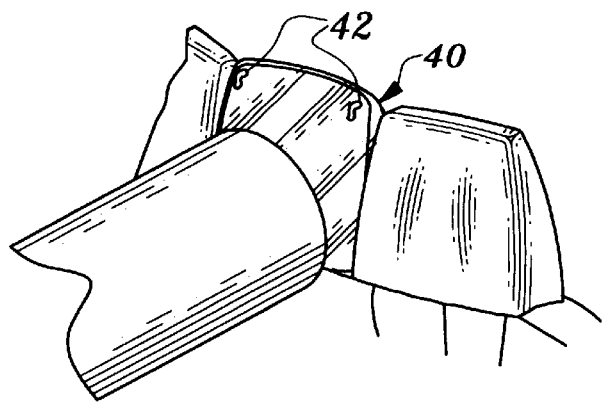
FIG. 8 illustrates application of the cap, or jacket, over the scaffold fitted to the tooth to be restored.

The cap 40 is, in accordance with the invention, fitted over the scaffold, and the pocket defined by the scaffold is filled with a suitable quantity of prepared composite material, as shown in FIG. 6. The scaffold is then placed over the previously prepared tooth T to be restored, as seen in FIG. 7.

Once the filled scaffold has been fitted to the tooth T, a small quantity of excess composite material M, together with any air that might have been entrapped in the mixture, will be forced out by hydraulic pressure through the vents 42. Also, in accordance with another aspect of the invention, there will be a layer, or a continuum of material, disposed within the confines of the opening 33, defining a film of composite material which transcends the opening 33, the thickness of which is determined by the area between the tooth T, the scaffold, and the cap disposed about the scaffold. Otherwise stated, the composite material M within the confines of the opening 33 will be compressed into the shape of the interior of the cap 40 and will, in accordance with the invention, completely cover the facial opening 33 of the scaffold and about the leading edge 28, thereby obliterating any hint of the scaffold which lies beneath the material. The obvious result is a restoration which, for all intents and purposes, has the appearance of being a normal tooth.

Figure 9:
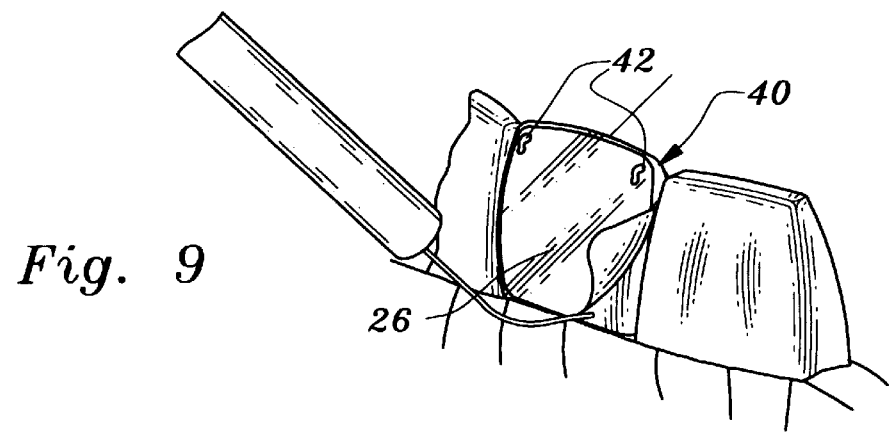
FIG. 9 illustrates removal of the cap once the composite material has cured.
Figure 10:
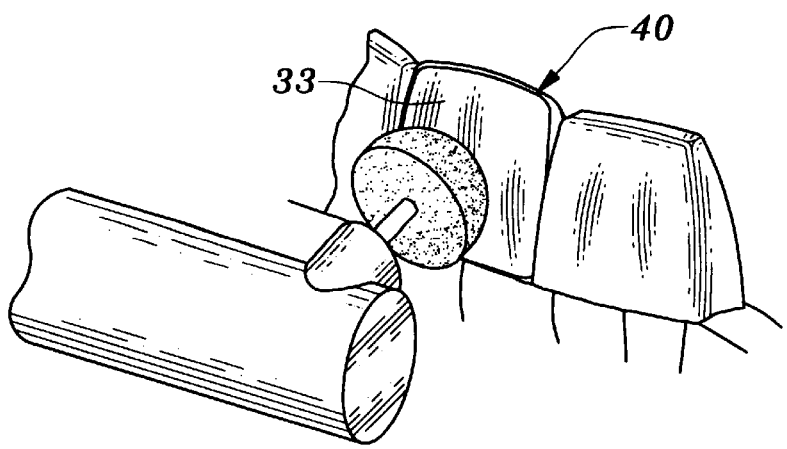
FIG. 10 illustrates the finishing and polishing process.
Figure 11:
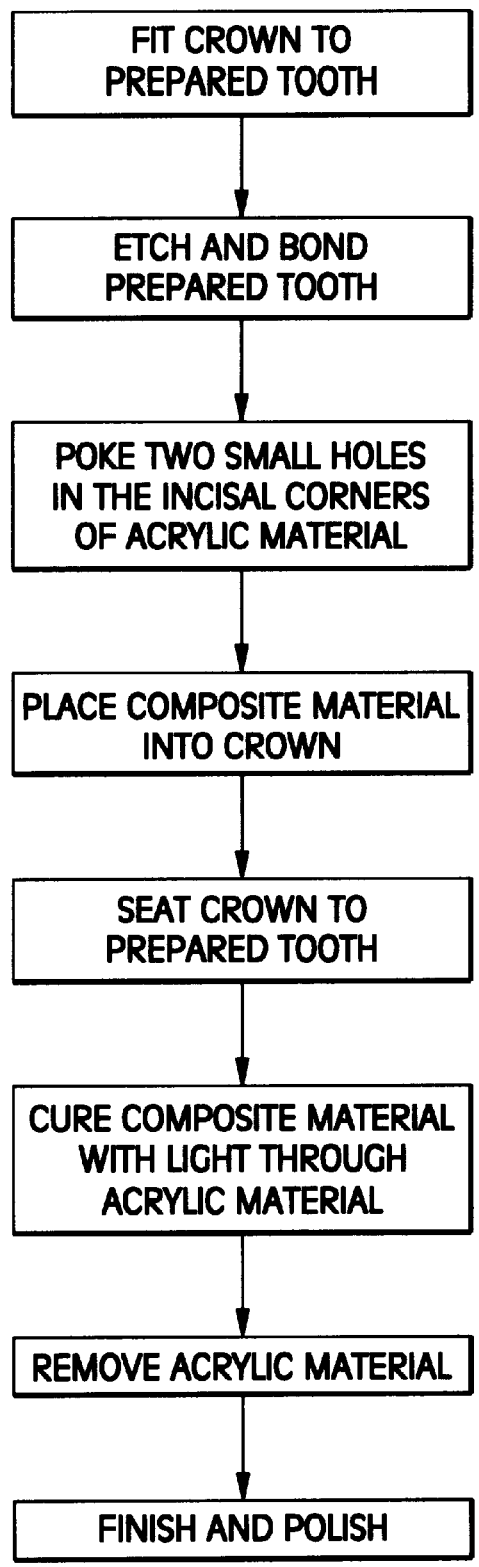
FIG. 11 is a diagram of the various steps in the process of creating the restoration of the present invention.

Once the composite material has cured, the cap, as seen in FIG. 9, is removed from the restoration, and as a final step in the creation of the prosthesis, the crown is polished and otherwise finished to provide an aesthetically pleasing and structurally strong restoration, which will last as long as the restored tooth remains and, because of the relatively nominal cost, can be discarded without undue concern when the primary tooth falls out or is removed.

Having thus disclosed a novel method of forming a crown for an anterior tooth to be restored, as well as the resultant crown, what is claimed as my invention is:

1. The method of creating an interim restorative crown for a previously damaged anterior tooth comprising the steps of:

fitting a scaffold about said anterior tooth wherein said scaffold defines a pocket, which pocket substantially conforms to the profile of said tooth;

forming an opening in the facial panel of said scaffold;

placing a cap over said scaffold;

adding a quantity of composite material to the interior pocket of said scaffold;

fitting said scaffold to said tooth such that composite material is forced through said opening and about at least a portion of the exterior of said scaffold;

removing said cap when said composite material is cured to thereby reveal an esthetically pleasing crown.

2. The novel method of claim 1, wherein said cap is vented to permit evacuation of excess composite material.

3. The novel method of claim 1, wherein at least one vent is formed in said cap, said vent being formed along the incisal corner thereof.

4. The novel method of claim 1, wherein said composite material is a dual-cure composite material.

5. The novel method of claim 1, wherein the opening in the facial panel of said scaffold includes substantially all of said facial panel.

6. The method of creating an interim restorative crown for a previously damaged anterior tooth comprising the steps of:

fitting a scaffold about said anterior tooth wherein said scaffold defines a pocket, which pocket substantially conforms to the profile of said tooth;

forming an opening in the facial panel of said scaffold;

placing a cap over said scaffold;

adding a quantity of composite material to the interior pocket of said scaffold;

fitting said scaffold to said tooth such that composite material is forced through said opening and about at least a portion of the exterior of said scaffold;

removing said cap when said composite material is cured to thereby reveal an esthetically pleasing crown;

finishing and polishing said crown.

7. The novel method of claim 6, wherein said cap is vented to permit evacuation of excess composite material.

8. The novel method of claim 6, Wherein at least one vent is formed in said cap, said vent being formed along the incisal corner thereof.

9. The novel method of claim 6, wherein said composite material is a dual-cure composite material.

* * * * *